US009907916B2

United States Patent
Evans et al.

(10) Patent No.: US 9,907,916 B2
(45) Date of Patent: Mar. 6, 2018

(54) LOW RADIAL PROFILE NEEDLE SAFETY DEVICE

(71) Applicant: West Pharmaceutical Services, Inc., Exton, PA (US)

(72) Inventors: Christopher Evans, Long Valley, NJ (US); Brian Costello, Whitehouse Station, NJ (US); Christopher Gieda, Long Valley, NJ (US)

(73) Assignee: WEST PHARMACEUTICAL SERVICES, INC., Exton, PA (US)

( * ) Notice: Subject to any disclaimer, the term of this patent is extended or adjusted under 35 U.S.C. 154(b) by 422 days.

(21) Appl. No.: 14/383,364

(22) PCT Filed: Mar. 7, 2013

(86) PCT No.: PCT/US2013/029518
§ 371 (c)(1),
(2) Date: Sep. 5, 2014

(87) PCT Pub. No.: WO2013/134465
PCT Pub. Date: Sep. 12, 2013

(65) Prior Publication Data
US 2015/0018773 A1 Jan. 15, 2015

Related U.S. Application Data

(60) Provisional application No. 61/607,711, filed on Mar. 7, 2012.

(51) Int. Cl.
*A61M 5/32* (2006.01)
*A61M 5/46* (2006.01)

(52) U.S. Cl.
CPC .......... *A61M 5/3272* (2013.01); *A61M 5/326* (2013.01); *A61M 5/3204* (2013.01);
(Continued)

(58) Field of Classification Search
CPC ............ A61M 5/3272; A61M 5/31585; A61M 5/31543
See application file for complete search history.

(56) References Cited

U.S. PATENT DOCUMENTS 4,425,120 A * 1/1984 Sampson ............ A61M 5/3271
604/198
4,731,059 A * 3/1988 Wanderer ............... A61B 5/155
600/577

(Continued)

FOREIGN PATENT DOCUMENTS

FR 2884723 A1 10/2006
JP 2014-059019 A 4/2014

(Continued)

OTHER PUBLICATIONS

Office Action dated Aug. 10, 2017 in U.S. Appl. No. 14/702,914, by Evans.

(Continued)

*Primary Examiner* — Bhisma Mehta
*Assistant Examiner* — Matthew A Engel
(74) *Attorney, Agent, or Firm* — Panitch Schwarze Belisario & Nadel LLP (57) ABSTRACT

A needle safety device (1) has an outer tube (10) within which a syringe barrel (2) is slideably receivable. A collar (14) in the outer tube (10) is moveable relative thereto and rotatably attachable to the distal end of the barrel (2). A force member (16) biases the outer tube (10) in a distal direction. A track (S) is formed in the inner surface of the outer tube (10). A pin (18) extending radially outwardly from the collar (14) slidingly engages the track (S). In a staging position, the barrel is inspectable. In a pre-injection position, the cannula extends a first length beyond the outer tube. In a full-insertion position, the cannula extends a second length (Continued)

greater than the first length beyond the outer tube. In a locked position, the cannula is entirely within the outer tube.

16 Claims, 9 Drawing Sheets

(52) U.S. Cl.
CPC ............ *A61M 5/3257* (2013.01); *A61M 5/46* (2013.01); *A61M 2005/3267* (2013.01)

(56) References Cited

U.S. PATENT DOCUMENTS

| | | | |
|---|---|---|---|
| 4,865,591 A | 9/1989 | Sams | |
| 4,894,055 A | 1/1990 | Sudnak | |
| 4,900,311 A * | 2/1990 | Stern | A61M 5/3271 604/198 |
| 4,917,673 A * | 4/1990 | Coplin | A61M 5/3271 604/198 |
| 4,923,446 A * | 5/1990 | Page | A61M 5/3243 604/198 |
| 4,966,592 A * | 10/1990 | Burns | A61M 5/3271 604/198 |
| 5,242,401 A | 9/1993 | Colsky | |
| 5,267,972 A | 12/1993 | Anderson | |
| 5,312,347 A | 5/1994 | Osborne et al. | |
| 5,346,480 A * | 9/1994 | Hess | A61M 5/3271 604/197 |
| 5,389,085 A | 2/1995 | D'Alessio et al. | |
| 5,472,430 A | 12/1995 | Vaillancourt et al. | |
| 5,569,190 A | 10/1996 | D'Antonio | |
| 5,573,513 A * | 11/1996 | Wozencroft | A61M 5/3257 128/919 |
| 5,591,138 A * | 1/1997 | Vaillancourt | A61M 5/3271 604/192 |
| 5,595,566 A * | 1/1997 | Vallelunga | A61M 5/3243 604/110 |
| 5,624,402 A | 4/1997 | Imbert | |
| 5,688,241 A * | 11/1997 | Asbaghi | A61M 5/326 604/110 |
| 5,785,691 A | 7/1998 | Vetter et al. | |
| 6,017,329 A | 1/2000 | Hake | |
| 6,027,482 A | 2/2000 | Imbert | |
| D430,293 S | 8/2000 | Jansen | |
| D431,864 S | 10/2000 | Jansen | |
| 6,183,446 B1 | 2/2001 | Jeanbourquin | |
| 6,190,364 B1 | 2/2001 | Imbert | |
| 6,196,998 B1 | 3/2001 | Jansen et al. | |
| 6,280,418 B1 | 8/2001 | Reinhard et al. | |
| D447,797 S | 9/2001 | Odell et al. | |
| D457,954 S | 5/2002 | Wallace et al. | |
| D461,244 S | 8/2002 | Niermann | |
| 6,432,088 B1 | 8/2002 | Huang et al. | |
| D468,016 S | 12/2002 | Mosler et al. | |
| 6,491,665 B1 | 12/2002 | Vetter et al. | |
| 6,491,667 B1 | 12/2002 | Keane et al. | |
| 6,520,935 B1 | 2/2003 | Jansen et al. | |
| 6,524,282 B1 | 2/2003 | Sudo et al. | |
| 6,547,764 B2 | 4/2003 | Larsen et al. | |
| 6,569,124 B1 | 5/2003 | Perouse | |
| 6,632,199 B1 | 10/2003 | Tucker et al. | |
| 6,648,858 B2 | 11/2003 | Asbaghi | |
| 6,776,777 B2 | 8/2004 | Barrelle | |
| 6,821,267 B2 | 11/2004 | Veillon, Jr. et al. | |
| 6,855,129 B2 | 2/2005 | Jensen et al. | |
| 6,884,237 B2 * | 4/2005 | Asbaghi | A61M 5/3272 604/192 |
| 6,926,697 B2 | 8/2005 | Malenchek | |
| 6,986,760 B2 | 1/2006 | Giambattista et al. | |
| 7,241,278 B2 | 7/2007 | Moller | |
| 7,314,464 B2 | 1/2008 | Giambattista et al. | |
| 7,374,555 B2 | 5/2008 | Heinz et al. | |
| D570,478 S | 6/2008 | Sudo | |
| D581,046 S | 11/2008 | Sudo | |
| D581,049 S | 11/2008 | Sudo | |
| 7,462,168 B2 | 12/2008 | Stonehouse et al. | |
| D589,612 S | 3/2009 | Sudo | |
| 7,497,847 B2 | 3/2009 | Crawford et al. | |
| D596,290 S | 7/2009 | Kawamura | |
| 7,648,481 B2 | 1/2010 | Geiger et al. | |
| 7,666,164 B2 | 2/2010 | Giambattista et al. | |
| 7,699,813 B2 | 4/2010 | Liversidge | |
| 7,806,861 B2 | 10/2010 | Witowski | |
| 7,828,777 B2 | 11/2010 | Vetter et al. | |
| RE42,355 E | 5/2011 | Heiniger | |
| 8,016,797 B2 | 9/2011 | Gratwohl et al. | |
| 8,052,653 B2 | 11/2011 | Gratwohl et al. | |
| 8,062,252 B2 | 11/2011 | Alheidt et al. | |
| 8,062,265 B2 | 11/2011 | Millerd | |
| 8,075,522 B2 | 12/2011 | Larsen et al. | |
| 8,128,594 B1 * | 3/2012 | Chang | A61M 5/3272 604/110 |
| 8,287,501 B2 | 10/2012 | Wei | |
| 8,303,541 B2 | 11/2012 | Chun | |
| 8,328,765 B2 | 12/2012 | Daily et al. | |
| 2001/0003150 A1 | 6/2001 | Imbert | |
| 2001/0031949 A1 * | 10/2001 | Asbaghi | A61M 5/326 604/198 |
| 2002/0004652 A1 * | 1/2002 | Asbaghi | A61M 5/326 604/242 |
| 2002/0133122 A1 | 9/2002 | Giambattista et al. | |
| 2003/0050609 A1 | 3/2003 | Sams | |
| 2003/0120209 A1 | 6/2003 | Jensen et al. | |
| 2003/0144630 A1 * | 7/2003 | Chang | A61M 5/3272 604/198 |
| 2004/0111064 A1 * | 6/2004 | Asbaghi | A61M 5/3272 604/198 |
| 2004/0215148 A1 | 10/2004 | Hwang et al. | |
| 2005/0075611 A1 | 4/2005 | Hetzler et al. | |
| 2005/0107740 A1 | 5/2005 | Jensen et al. | |
| 2005/0113750 A1 | 5/2005 | Targell | |
| 2006/0189933 A1 * | 8/2006 | Alheidt | A61M 5/326 604/110 |
| 2008/0262436 A1 * | 10/2008 | Olson | A61M 5/2033 604/198 |
| 2009/0005742 A1 * | 1/2009 | Liversidge | A61M 5/326 604/263 |
| 2009/0024093 A1 * | 1/2009 | Carrel | A61M 5/326 604/198 |
| 2009/0149816 A1 | 6/2009 | Hetzler et al. | |
| 2010/0094207 A1 | 4/2010 | Boyd et al. | |
| 2010/0198163 A1 | 8/2010 | Bonnet | |
| 2010/0262083 A1 | 10/2010 | Grunhut et al. | |
| 2010/0268170 A1 * | 10/2010 | Carrel | A61M 5/2033 604/198 |
| 2010/0286623 A1 * | 11/2010 | Liversidge | A61M 5/326 604/198 |
| 2010/0298779 A1 | 11/2010 | Hetzler et al. | |
| 2011/0015578 A1 | 1/2011 | Lowke | |
| 2011/0046563 A1 | 2/2011 | Vetter et al. | |
| 2011/0054411 A1 | 3/2011 | Dowds et al. | |
| 2011/0112486 A1 | 5/2011 | Grimard | |
| 2011/0118667 A1 * | 5/2011 | Zaiken | A61M 5/3202 604/138 |
| 2011/0137261 A1 | 6/2011 | Garber et al. | |
| 2011/0319832 A1 * | 12/2011 | Chun | A61M 5/326 604/198 |
| 2011/0319833 A1 * | 12/2011 | Chun | A61M 5/326 604/198 |
| 2012/0041368 A1 * | 2/2012 | Karlsson | A61M 5/3272 604/111 |
| 2012/0253289 A1 | 10/2012 | Cleathero | |
| 2012/0277724 A1 | 11/2012 | Larsen et al. | |
| 2012/0310206 A1 | 12/2012 | Kouyoumjian et al. | |
| 2012/0316508 A1 | 12/2012 | Kirchhofer | |
| 2012/0323186 A1 | 12/2012 | Karlsen et al. | |
| 2013/0204186 A1 * | 8/2013 | Moore | A61M 5/2448 604/111 |
| 2013/0211338 A1 * | 8/2013 | Roberts | A61M 5/326 604/198 |
| 2013/0324923 A1 | 12/2013 | Roberts et al. | |
| 2014/0012208 A1 | 1/2014 | Plumptre et al. | |

(56) References Cited

U.S. PATENT DOCUMENTS

FOREIGN PATENT DOCUMENTS

| WO | 9014112 A1 | 11/1990 |
| WO | 2009137845 A1 | 11/2009 |
| WO | 2015022787 A1 | 2/2015 |

OTHER PUBLICATIONS

Int'l Search Report and Written Opinion dated Jun. 24, 2013 in Int'l, Application No. PCT/US2013/029518.

* cited by examiner

Fig. 15A  Fig. 15B  Fig. 15C  Fig. 15D

LOW RADIAL PROFILE NEEDLE SAFETY DEVICE

CROSS-REFERENCE TO RELATED APPLICATION

This application is a section 371 of International Application No. PCT/US2013/029518, filed Mar. 7, 2013, which was published in the English language on Sep. 12, 2013 under International Publication No. WO 2013/134465 A1 which claims the benefit of U.S. Provisional Patent Application No. 61/607,711, filed Mar. 7, 2012, the disclosures of which are incorporated herein by reference.

BACKGROUND OF THE INVENTION

The present invention is directed to a low radial profile needle safety shield for syringes, in general, and for pharmaceutical syringes in particular.

Needlestick injuries are a well known occupational hazard for healthcare workers. Unintended needlesticks have the potential for transmitting blood-borne viruses such as hepatitis B and C and the human immunodeficiency virus (HIV) to the recipient. After a needlestick injury, certain procedures must be followed to minimize the risk of infection for the recipient, such as laboratory blood tests and post-exposure prophylaxis started immediately after exposure to a pathogen, such as one of the aforementioned viruses, in order to prevent infection by the pathogen and the development of the associated disease.

Conventional safety devices intended to reduce the frequency of post-injection needlesticks typically have a sheath partially or completely surrounding the pharmaceutical syringe. The sheath may be held in a retracted position exposing the needle for aspiration and injection and may be automatically deployed around a needle afterwards.

Among the drawbacks of many conventional prior art needle safety devices is that they are not compatible with current accepted practice due to sizes and configurations that are incompatible with conventional filling and sterilization equipment and methods.

Accordingly, there is a need in the art for a safety injection device having a low radial profile.

BRIEF SUMMARY OF THE INVENTION

Briefly stated, one aspect of the invention is a needle safety device for an injection device having a generally cylindrical barrel with a distal end from which a cannula extends. The needle safety device comprises an outer tube within which the barrel is slideably receivable. The outer tube has a distal end, a proximal end spaced from the distal end and a longitudinal axis. A collar in the outer tube is moveable relative thereto and is rotatably attachable to the distal end of the barrel. A force member is between the outer tube and the collar and biases the outer tube in a distal direction. A track S is formed in the inner surface of the outer tube. A pin extending radially outwardly from the collar 14 slidingly engages the track S. The track S comprises a assembly track segment extending from a staging position to a pre-injection position. The proximal end of the outer tube is in a position relative to the distal end of the barrel allowing the barrel to be inspected when the collar is attached to the distal end of the barrel and the pin is releasably retained in the staging position by a assembly catch in the outer tube. The cannula extends a first length beyond the distal end of the outer tube when the collar is attached to the distal end of the barrel and the pin is releasably retained in the pre-injection position by a first catch in the outer tube. A first track segment contiguous with the assembly track segment extends from the pre-injection position to a full-insertion position. The cannula extends a second length greater than the first length from the distal end of the outer tube when the collar is attached to the distal end of the barrel and the pin is in the full-insertion position. A second track segment contiguous with the first track segment extends from the full-insertion position to a locked position in which the pin is immovably retainable in a portion of the second track segment spaced from and parallel to a portion of the assembly track segment. The cannula is entirely within the outer tube when the collar is attached to the distal end of the barrel and the pin is immovably retained in the locked position by a second catch in the outer tube.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIGS. 15A-15D is a sequence of side elevation views of the safety device and a portion of a pharmaceutical syringe of FIG. 1 showing progressive positions of the safety device relative to the pharmaceutical insertion device.

DETAILED DESCRIPTION OF THE INVENTION

Reference will now be made in detail to embodiments of the invention, examples of which are illustrated in the accompanying drawings. The terminology used in the description of the invention herein is for the purpose of describing particular embodiments only and is not intended to be limiting of the invention.

As used in the description of the invention and the appended claims, the singular forms "a", "an" and "the" are intended to include the plural forms as well, unless the context clearly indicates otherwise. The words "and/or" as used herein refers to and encompasses any and all possible combinations of one or more of the associated listed items. The words "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The words "right," "left," "lower" and "upper" designate directions in the drawings to which reference is made. The words "inwardly" and "outwardly" refer to directions toward and away from, respectively, the geometric center of the needle safety shield, and designated parts thereof. The terminology includes the words noted above, derivatives thereof and words of similar import.

Although the words first, second, etc., are used herein to describe various elements, these elements should not be limited by these words. These words are only used to distinguish one element from another. For example, a first segment could be termed a second segment, and, similarly, a second segment could be termed a first segment, without departing from the scope of the present invention.

As used herein, the word "distal" means in a direction away from the hand of a user holding the injection device immediately prior to injecting a medicament (e.g., the end of the barrel from which the cannula extends is the distal end of the barrel) and "proximal" means toward the hand of a user holding the injection device immediately prior to injecting a medicament.

The following descriptions are directed towards various embodiments of a needle safety shield in accordance with the present invention.

Referring to the drawings in detail, where like numerals indicate like elements throughout, there is shown in FIGS. 1-7 a preferred embodiment of a low radial profile needle safety device, generally designated 10, and hereinafter referred to as the "safety device" 10 in accordance with the present invention. The safety device 10 is for use with an injection device 1, such as a pharmaceutical syringe. The injection device 1 may be a pre-filled; however, the present invention is not so limited. For example, the injection device 1 may be nearly any type of pharmaceutical syringe, including those to be filled by a patient or user, for example.

The injection device 1 preferably has a generally cylindrical barrel 2 having a distal end 2a and an opposing proximal end 2b. A cannula (or needle) 3 extends from the distal end 2a of the barrel 2 and is in fluid communication with a bore of the barrel 2. The cannula 3 may be removably attached to the distal end 2a of the barrel 2. Alternatively, and preferably, the cannula 3 is fixedly attached thereto. A removable shield 4 covers the cannula 3. Typically, the distal end 2a of the barrel 2 is configured as a tapered hub 5 that may have a variety of configurations, such as an inverted frustum, a cylinder or a sphere. Preferably, the hub 5 has a generally circular or bulbous shape that extends radially outwardly or beyond at least some other portion of the distal end 2a of the barrel 2. However, the hub 5 is not limited to the size, shape and/or configuration shown and described herein Although the barrel 2 may be formed of nearly any material capable of safely enclosing medicaments, it is preferably formed of glass or a polymeric material. The injection device 1 may be pre-filled with a medicament or may be provided without a medicament for filling by the user.

A piston rod and piston (not shown) are slidably receivable in the bore of the barrel 2. The piston rod may have a free proximal end that extends from the proximal end of the barrel.

The safety device 10 comprises an outer tube 12 within which the barrel 2 is slideably receivable. The outer tube 12 has a distal end 12a, a proximal end 12b and a longitudinal axis A. A collar 14 is in the outer tube 12 and is movable relative thereto. In some embodiments, the collar 14 is fixedly attachable to the distal end 2a of the barrel 2. In other embodiments, the collar 14 is rotatably attachable to the distal end 2a of the barrel 2. A force member 16, such as a compressible coil spring, is provided between the outer tube 12 and the collar 14. The force member biases the outer tube 12 in a distal direction. A track S is formed in the inner surface of the outer tube 12. A pin 18 extending radially outwardly from the collar 14 slidingly engages the track S which, in turn, guides the movement of the pin 18 and therefore the collar 14 within the outer tube 12.

Figure 7:
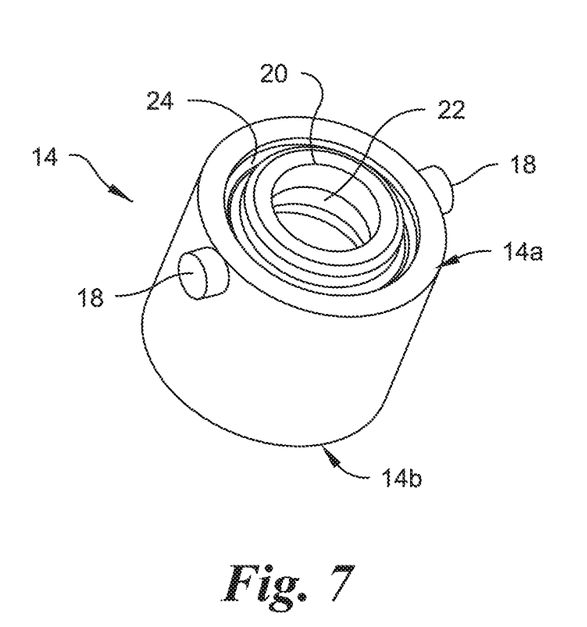
FIG. 7 is a top perspective view of the collar of the safety of FIG. 1.
Figures 8, 9:
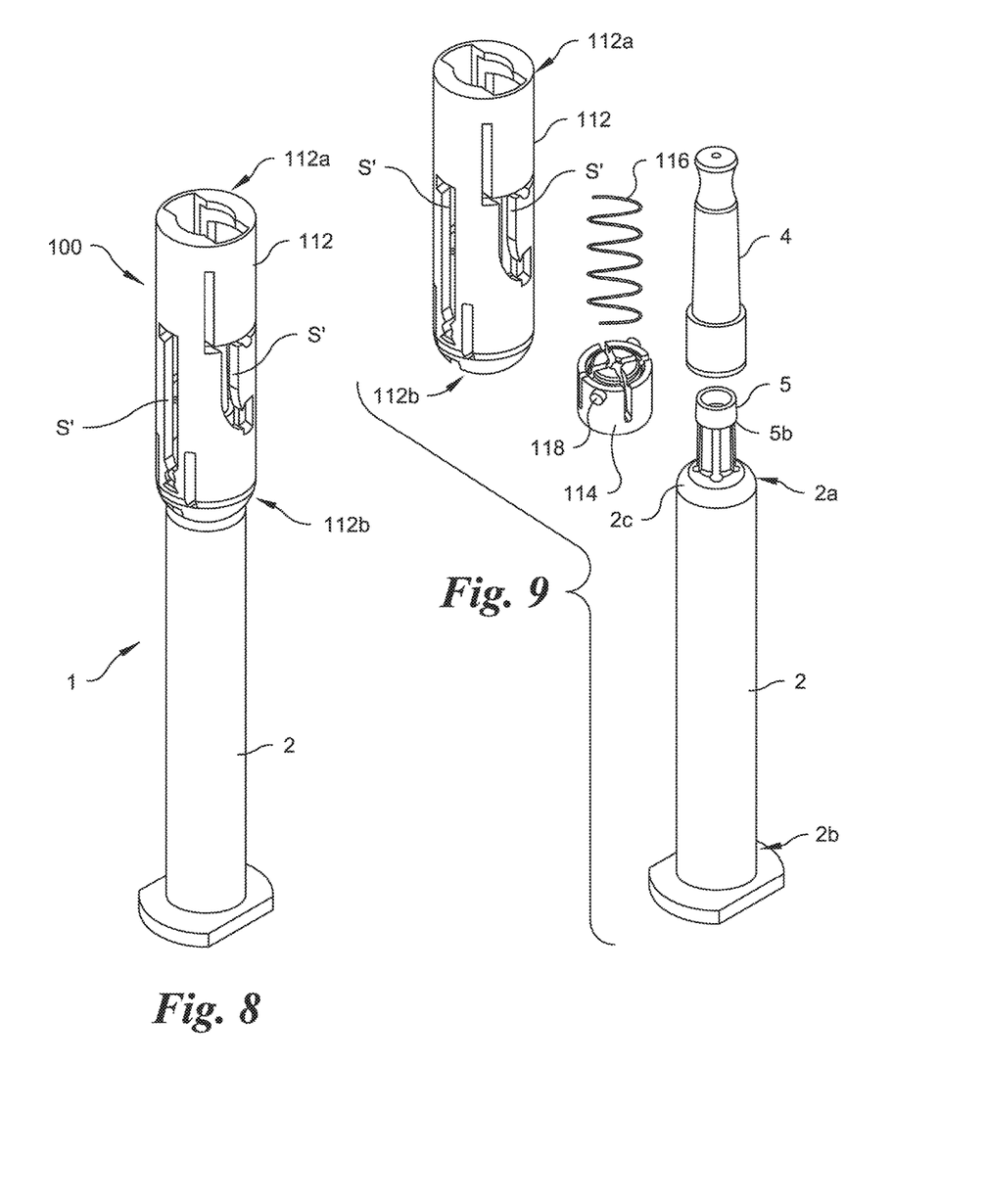
FIG. 8 is a side perspective view of another embodiment of the low radial-profile needle safety device in a staging position on the barrel of a pharmaceutical injection device in accordance with the present invention.
FIG. 9 is an exploded side perspective view of the needle safety device of FIG. 8.
Figure 10:
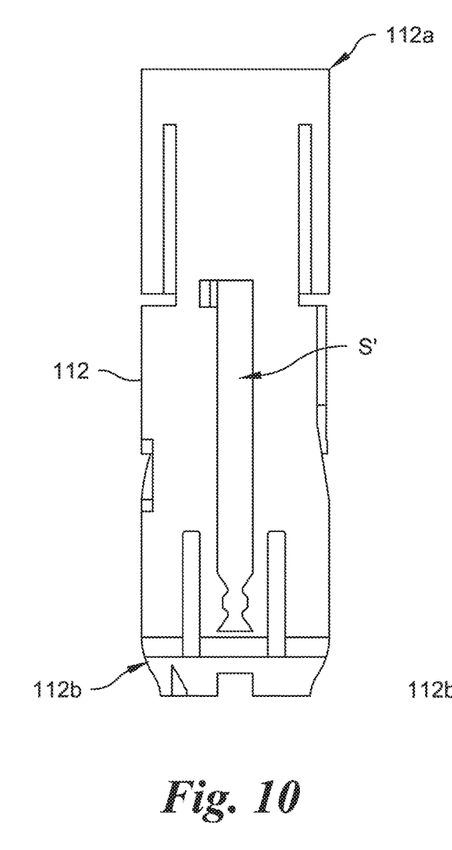
FIG. 10 is an side elevational view of the outer tube of the safety device of FIG. 8.
Figure 11:
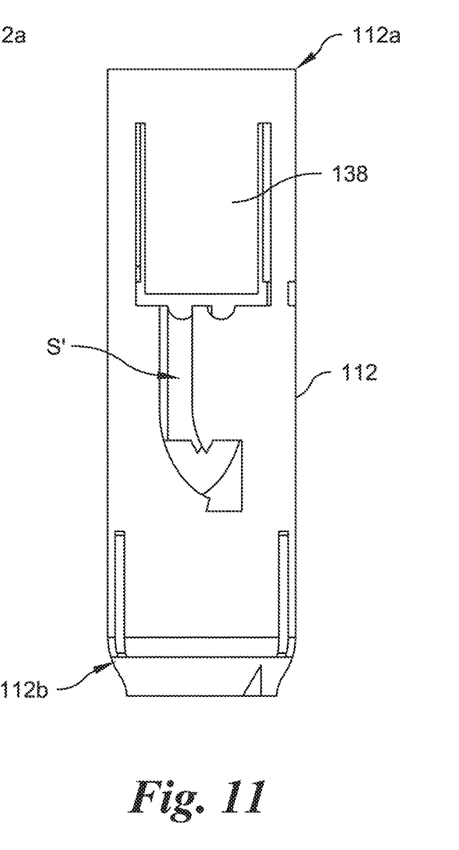
FIG. 11 is a front elevation view of the outer tube of the safety device of FIG. 8.

Referring to FIG. 7, in a preferred embodiment, the collar 14 has the general shape of a hollow cylinder terminating at the distal end with an annulus 20 having a central bore 22 sized to receive and retain the distal end 2a of the barrel 2 or the hub 5 if the distal end 2a of the barrel 2 is configured as a hub. The annulus 20 is sufficiently compliant and sized to allow passage of the hub 5 through the bore 22 and then to rotatably engage the hub 5. The outer surface of the annulus 20 has a generally circular channel 24 to receive one end of the force member (e.g., a coil spring) 16. A circumferential step 26 (see, FIG. 3) in the inner surface of the outer tube 12 is sized to receive and engage the distal end of the force member 16. At least one pin 18 extends radially outwardly form the collar 18 and is slidably receivable in the track S. In embodiments in which the outer tube 12 has a plurality of tracks, the collar 14 may have a corresponding plurality of pins.

To mount the collar 14 to the barrel 2, the distal end 2a of the barrel 2 or the hub 5 may be inserted into and through the proximal end 14b of the collar 14 and into and through the distal end 14a of the collar 14. As the hub 5 passes through the distal end 14a of the collar 14, the bore 22 in the annulus 20 expands until the hub 5 passes completely therethrough. The annulus 20 then return to its initial state in which the distal end 14a of the collar 14 abuts the proximal surface 5b of the hub 5, thereby rotatably attaching the collar 14 on the barrel 2 between the hub 5 and a shoulder 2c or enlarged portion of the distal end 2a of the barrel 2.

Figure 1:
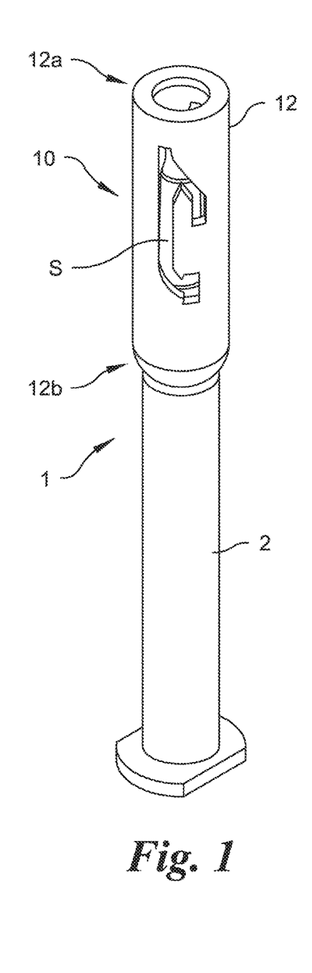
FIG. 1 is a side perspective view of an embodiment of the low radial-profile needle safety device in a staging position on the barrel of a pharmaceutical injection device in accordance with the present invention.
Figure 2:
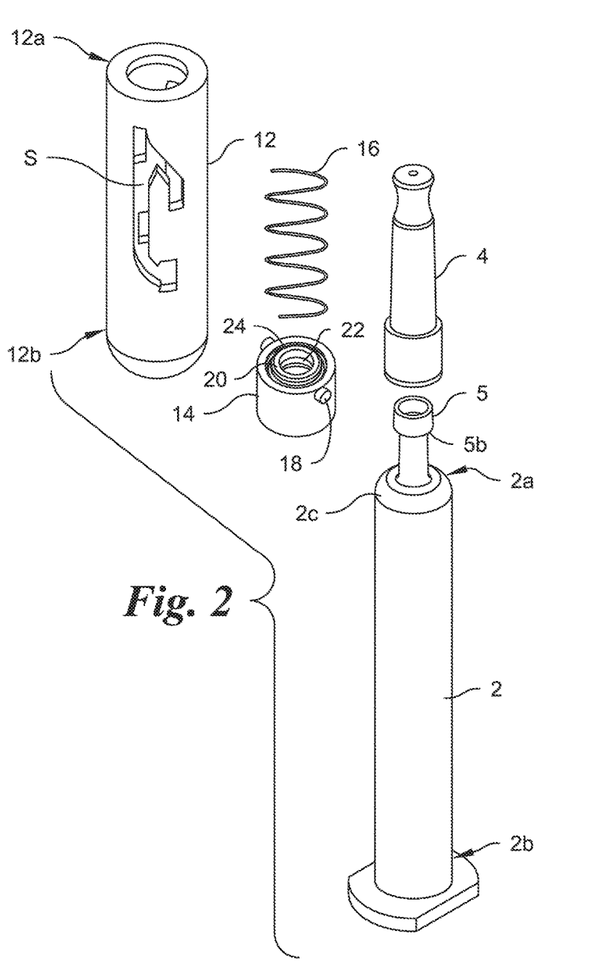
FIG. 2 is an exploded side perspective view of the needle safety device of FIG. 1.
Figure 3:
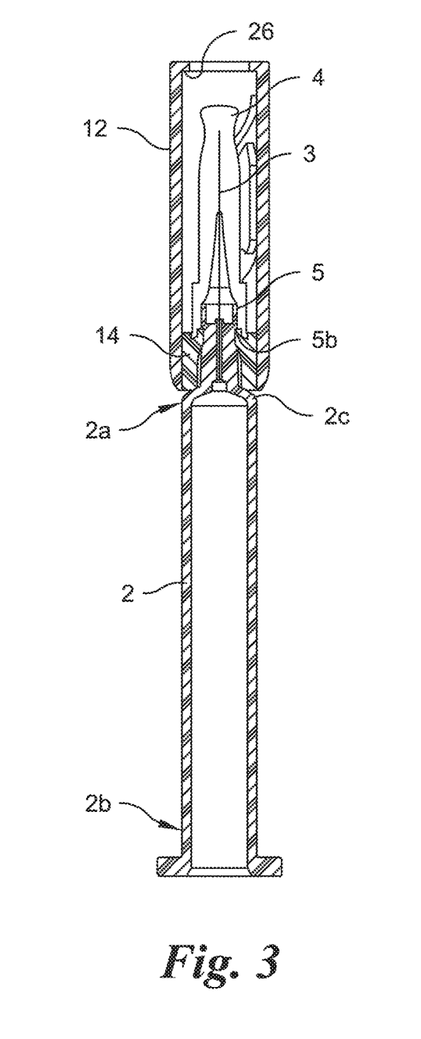
FIG. 3 is an side cross-sectional view of the safety device of FIG. 1.
Figure 4:
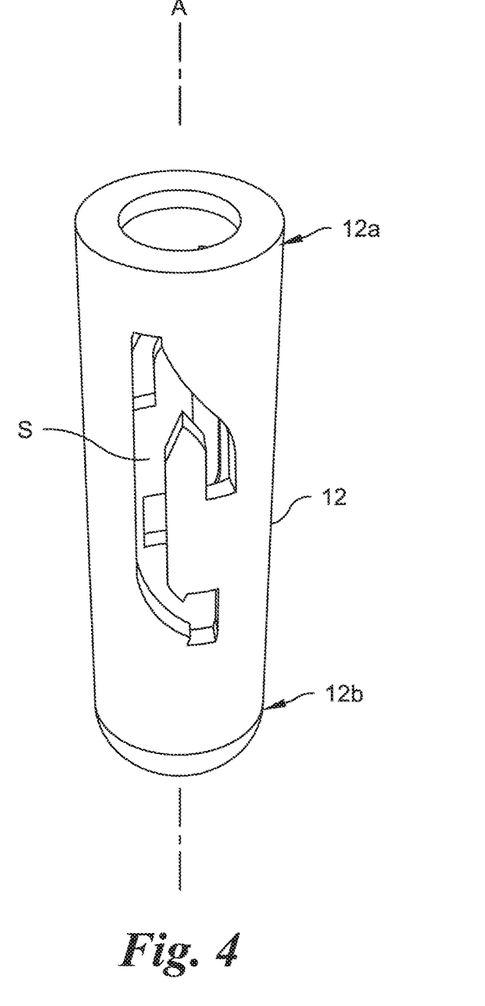
FIG. 4 is a side perspective view of the outer tube of the safety device of FIG. 1.
Figure 5:
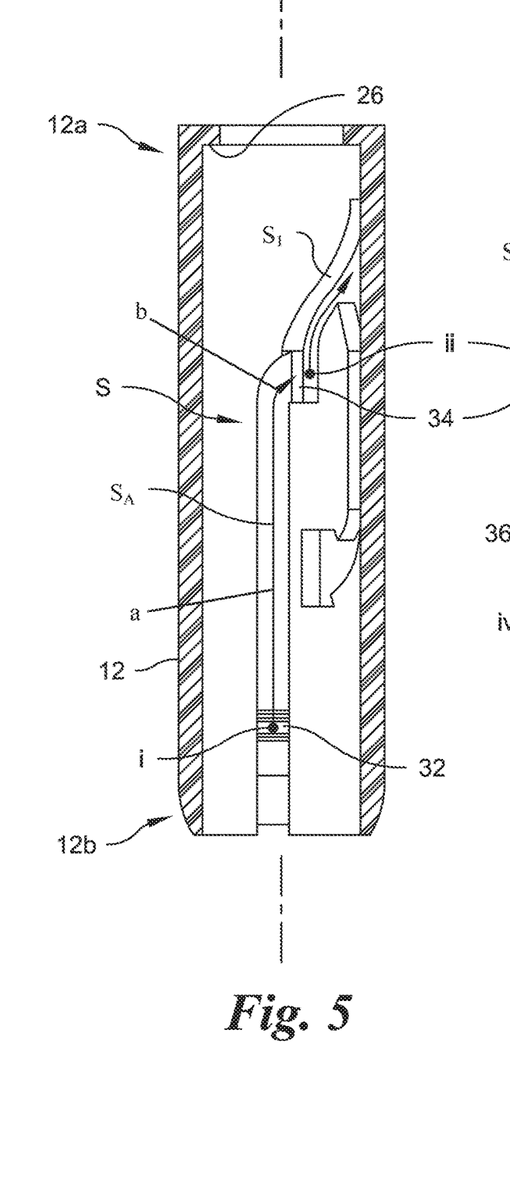
FIGS. 5 and 6 are side cross-sectional views of the outer tube of the safety device of FIG. 1 showing the track in the outer tube.
Figure 6:
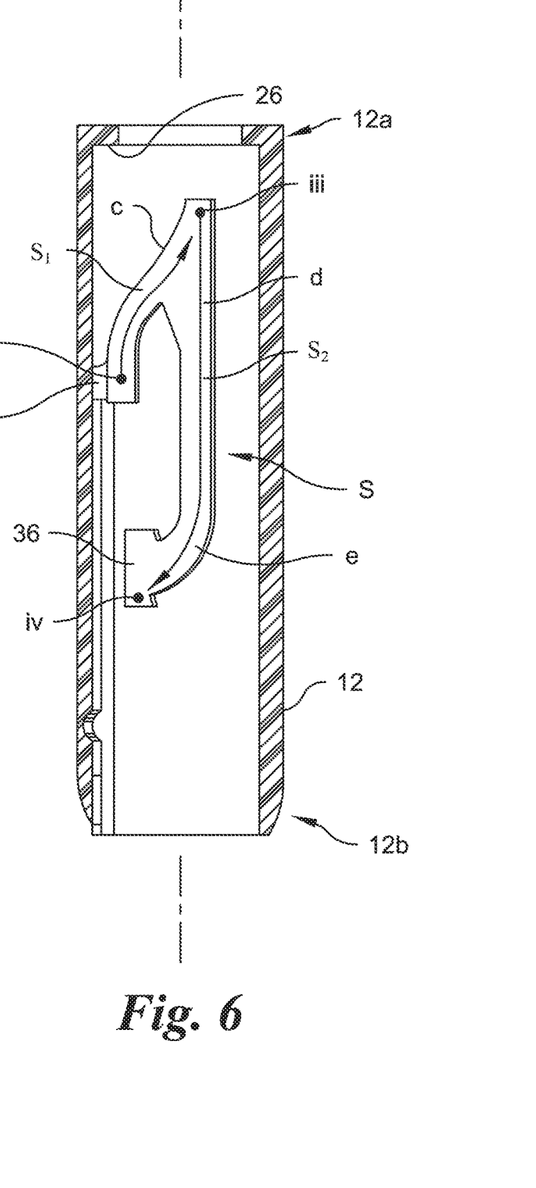
Figure 15A:
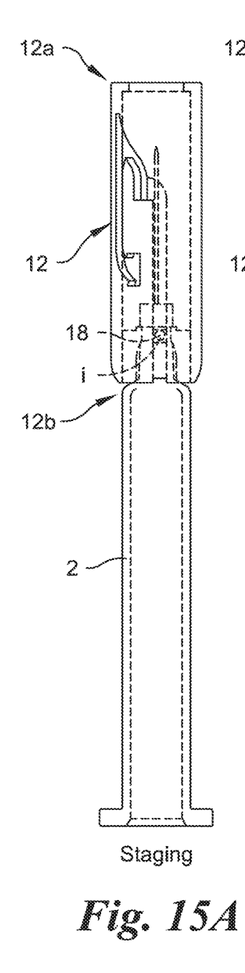

Referring to FIGS. 5 and 6, in some embodiments, the track S comprises three track segments. An assembly track segment $S_A$ is provided to allow the safety device 10 to be assembled and inspected after the collar 14 has been attachment to the distal end 2a of the barrel 2 as discussed above. The assembly track segment $S_A$ extends from a staging position (i) shown in FIGS. 5, 12 and 15A having a assembly catch 32 to a pre-injection position (ii) shown in FIGS. 5, 6, 13 and 15B having a first catch 34 and has as a profile including an initial portion (a), (a') substantially parallel to the longitudinal axis A of the outer tube 12 followed by a final portion (b), (b') angled with respect to the longitudinal axis A and serving as a cammed surface. When the collar 14 is attached to the distal end 2a of the barrel 2 and the pin 18 is in the staging position (i), the proximal end 12b of the outer tube 12 is in a position relative to the distal end 2a of the barrel 2 allowing the barrel 2 to be inspected.

During the assembly process, the force element 16 is inserted in the outer tube 12. The collar 14, attached to the distal end 2a of the barrel 2, is then inserted in the outer tube 12 such that the pin 18 (or plurality of pins, if there is a plurality of tracks) is in the assembly track segment $S_A$ (or plurality of assembly track segments). The outer tube 12 is moved in the proximal direction causing an initial compression of the force element 16 as the pin 18 travels to the beginning of the assembly track segment $S_A$ and becomes releasably retained in the assembly catch 32 thereby securing the outer tube 12 in the staging position (i).

As the outer tube 12 moves in the proximal direction causing the force member 16 to be compressed, the pin 18 travels the initial portion of the assembly track segment $S_A$ and is guided to the pre-injection position (ii) by the cammed surface which imparts an angular rotation to the collar releasably securing the pin 18 in the first catch 34. When the collar 14 is attached to the distal end 2a of the barrel 2 and the pin 18 is in the first catch 34, the cannula 3 extends a first length $L_1$ beyond the distal end of the outer tube 12. The first length $L_1$ of cannula extension depends on the particular size and configuration of the insertion device 1. At a minimum the first length $L_1$ of extension allows visualization of the distal most tip of the cannula 3 at an insertion location prior to penetration of the skin.

Figures 15B, 15C, 15D:
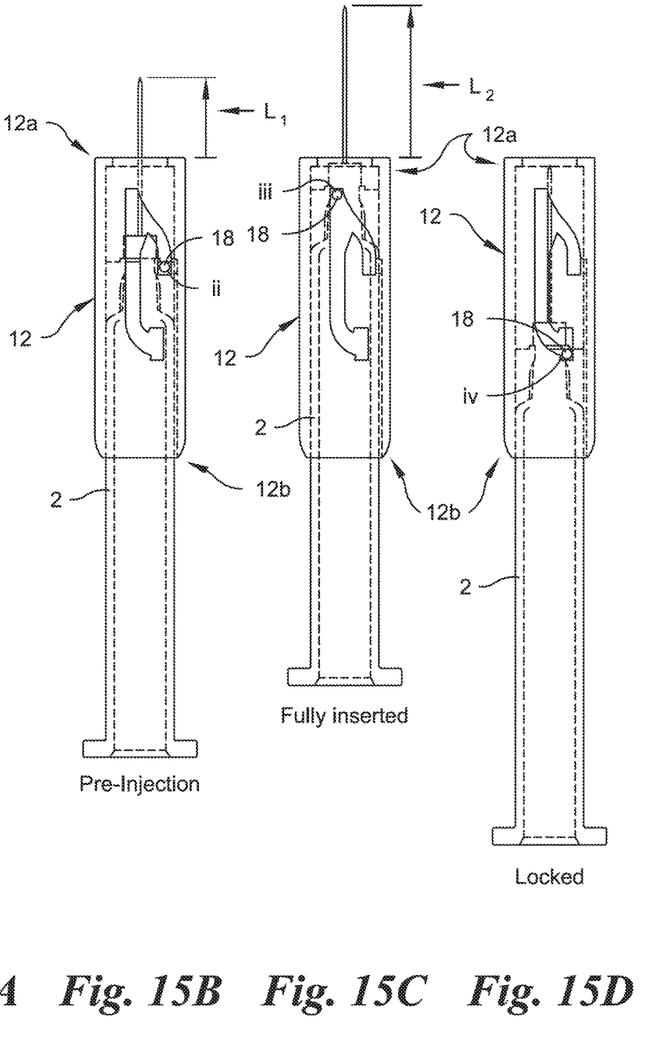

A first track segment $S_1$ contiguous with the assembly track segment $S_A$ extends from the pre-injection position (ii) to a full-insertion position (iii) shown in FIGS. 5, 6 and 15C. The first track segment $S_1$ is angled with respect to the longitudinal axis A of the outer tube 12 and has an arcuate profile (c).

At the initiation of an injection, the distal end 12a of the outer tube 12 makes contact with the skin. The force applied by the skin to the outer tube 12 moves the pin 18 out of the assembly catch 32 and along the beginning of the first track segment $S_1$. As the skin is being penetrated by the cannula 3, continued application of force by the skin to the outer tube 12 further moves the outer tube 12 in the proximal direction and the pin 18 in the distal direction along the first track segment $S_1$ to the fully inserted position (iii). When the collar 14 is attached to the distal end 2a of the barrel 2 and the pin 18 is in the full-insertion position (iii), the cannula 3 extends a second length $L_2$ greater than the first length $L_1$ from the distal end 12a of the outer tube 12. The second length $L_2$ of the cannula extension at the full-insertion position (iii) depends on the particular size and configuration of the insertion device 1 and the subcutaneous location to which the medicament is to be delivered. The first track segment $S_1$ guides the pin 18 along a generally arcuate path imparting both axial translation and rotation to the collar 14. The outer tube 12 remains in the full-insertion position (iii) until withdrawal of the cannula 3 is initiated, typically after a full dose of the medicament is delivered.

Figure 13:
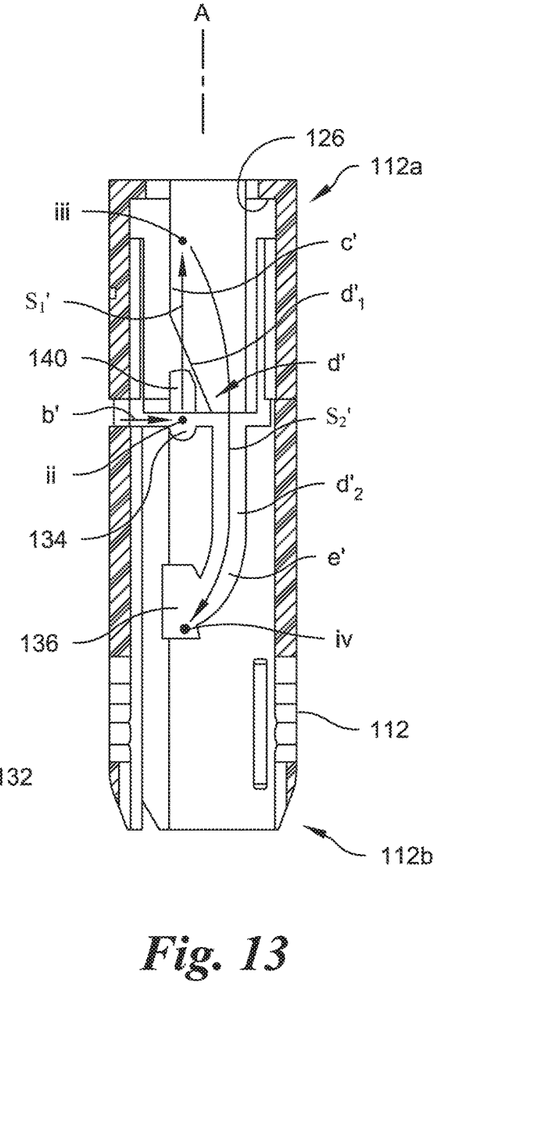
FIG. 13 is a side cross-sectional view of the outer tube of the safety device of FIG. 8.

A second track segment $S_2$ contiguous with the first track segment $S_1$ extends from the full-insertion position (iii) to a locked position (iv) shown in FIGS. 6, 13 and 15D having a second catch 36 in which the pin 18 is immovably retainable. The second track segment $S_2$ has an initial portion (d) extending from the full-insertion position (iii) substantially parallel to the longitudinal axis A of the outer tube 12 followed by an arcuate profile (e) providing a cammed surface terminating in an axially extending locked position (iv). As the cannula 3 is being withdrawn after the desired dose of medicament has been delivered, the force applied by the skin to the outer tube 12 decreases and the outer tube 12 moves in the distal direction relative to the collar 14 under the reactive force of the force member 16 compressed between the collar 14 and the outer tube 12. The second track segment $S_2$ initially guides the pin 18 substantially parallel to the longitudinal axis A and then along a generally arcuate path imparting both axial translation and a rotation to the collar and finally into the locked position (iv). When the collar 14 is attached to the distal end 2a of the barrel 2 and the pin 18 is immovably retained in the second catch 36, the outer tube 12 fully covers the cannula 3 in the entirety and is prevented from moving in either the proximal or distal directions.

As the outer tube 12 moves in the proximal direction causing the force member 16 to be compressed, the pin 18 travels the initial portion of the first track segment $S_1$ and is guided to the pre-injection position (ii) by the cammed surface which imparts an angular rotation to the collar releasably securing the pin 18 in second catch 34 When the collar 14 is attached to the distal end 2a of the barrel 2 and the pin 18 is in the second catch 34, the cannula 3 extends a first length $L_1$ beyond the distal end of the outer tube 12. The length L1 of cannula extension depends on the particular size and configuration of the insertion device 1. At a minimum the length of extension allows visualization of the distal most tip of the cannula 3 at an insertion location prior to penetration of the skin.

A second track segment $S_2$ contiguous with the first track segment $S_1$ extends from the pre-injection position (ii) to a full-insertion position (iii) shown in FIG. 15C. The second track segment $S_2$ is angled with respect to the longitudinal axis of the outer tube 12 and has an arcuate profile (c).

At the initiation of an injection, the distal end 12a of the outer tube 12 makes contact with the skin. The force applied by the skin to the outer tube 12 moves the pin 18 out of the first catch 32 and along beginning of the second track segment $S_2$. As the skin is being penetrated by the cannula 3, continued application of force by the skin to the outer tube 12 further moves the outer tube 12 in the proximal direction and the pin 18 in the distal direction along the second track segment $S_2$ to the fully inserted position (iii). When the collar 14 is attached to the distal end 2a of the barrel 2 and the pin 18 is in the full-insertion position (iii), the cannula 3 extends a second length $L_2$ greater than the first length $L_1$ from the distal end 12a of the outer tube 12. The length L2 of cannula extension at the full-insertion position (iii) depends on the particular size and configuration of the insertion device 1 and the subcutaneous location the medicament is to be delivered. The second track segment guides the pin 18 along a generally arcuate path imparting both axial translation and rotation to the collar 14. The outer tube 12 remains in the full-insertion position (iii) until withdrawal of the cannula 3 is initiated, typically after a full dose of the medicament is delivered.

A third track segment $S_3$ contiguous with the second track segment $S_2$ extends from the full-insertion position (iii) to a locked position (iv) shown in FIG. 15D having a third catch 36 in which the pin 18 is immovably retainable. The third track segment $S_3$ has an initial portion (d) extending from the full-insertion position (iii) substantially parallel to the longitudinal axis of the outer tube followed by an arcuate profile (e) providing a cammed surface terminating in an axially extending locked position (iv). As the cannula 3 is being withdrawn after the desired dose of medicament has been delivered, the force applied by the skin to the outer tube 12 decreases and the outer tube 12 moves in the distal direction relative to the collar 14 under the reactive force of the force member 16 compressed between the collar and the outer tube. The third track segment $S_3$ initially guides the pin 18 substantially parallel to the longitudinal axis and then along a generally arcuate path imparting both axial translation and a rotation to the collar and finally into the locked position (iv). When the collar 14 is attached to the distal end 2a of the barrel 2 and the pin 18 is immovably retained in the third catch 36, the outer tube 12 fully covers the cannula 3 in the entirety and is prevented from moving in either the proximal or distal directions.

Referring to the drawings in detail, where like numerals indicate like elements throughout, there is shown in FIGS. 8-14 another preferred embodiment of a low radial profile needle safety device, generally designated 100, and hereinafter referred to as the "safety device" 100 in accordance with the present invention. The safety device 100 is also for use with the injection device 1 disclosed above.

The safety device 100 comprises an outer tube 112 configured to slidably receive therein a portion of the distal end 2a of the barrel 2. At least one track S' is formed in the inner surface of the outer tube 112. The at least one track S' has a plurality of contiguous segments further discussed below. In some embodiments, the inner surface may have a plurality of tracks, each having the same configuration, positioned in a spaced-apart, aligned arrangement. A portion of the outer tube 112 has a generally U-shaped cut therethrough forming a flexible tongue 138 having a radially disposed ramp 140.

A collar 114 is slidably received in the outer tube 112. The collar 114 is attachable to the distal end 2a of the barrel 2. At least one pin 118 extends radially outwardly from a sidewall of the collar 114 and is slidably received in the at least one track S' formed in the inner surface of the outer tube 112. In embodiments in which the outer tube 112 may have a plurality of tracks S', the collar 114 may have a corresponding plurality of pins 118 projecting radially outwardly from spaced-apart locations around the circumference of the sidewall. A force member 116 extending between the outer tube 112 and the collar 114 biases the outer tube 112 in a distal direction. In some embodiments, opposed ends of the force member 116 may be received and retained in a circumferential channel 124 in the outer surface of the collar 114 and a circumferential step 126 in the inner surface of the distal end 112a of the outer tube 112.

Figure 14:
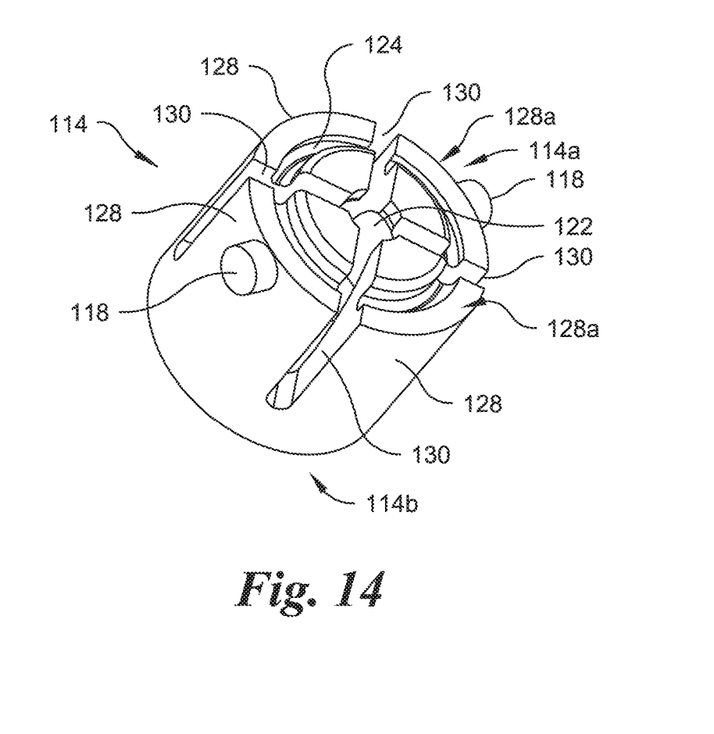
FIG. 14 is a top perspective view of the collar of FIG. 8.

Referring to FIG. 14, in a preferred embodiment, the collar 114 is a body of revolution having a bore 122 therethrough and includes at least one and preferably four spaced-apart fingers 128 fixedly attachable to the distal end 2a of the barrel 2. Each finger 128 is sufficiently compliant to allow passage of the hub 5 through the bore 122 of the collar 114 and then to return to an initial configuration. Each finger 128 preferable is configured to conform to the size and/or shape of a corresponding portion of the distal end 2a of the barrel 2. A gap or spacing 130 is preferably located between adjacent fingers 128, which allows for the collective expansion and contraction of the four fingers 128.

A channel 124 formed in the distal end 128a of each finger 128 collectively forms the circular channel 124 in the outer surface of the collar 114 to receive one end of the force element 116. A circumferential step 126 (see, FIGS. 12 and 13) in the inner surface of the outer tube 112 is sized to receive and engage the distal end of the force member 116. Diametrically opposed pins 118 extend radially outwardly from the collar 114 and are sized to slidingly engage the at least one track S' formed in the inner surface of the outer tube 112.

To mount the collar 114 to the barrel 2, the hub 5 may be inserted into and through the proximal end 114b of the collar 114 and into and through the distal end 114a of the collar 114. As the hub 5 passes through the distal end 114a of the collar 114, each of the fingers 128 may flex radially outwardly from the longitudinal axis A until the hub 5 passes completely therethrough. The fingers 128 then return to their initial state in which the distal end 128a of each finger 128 abuts the proximal surface 5b of the hub 5, thereby immovably attaching the collar 114 in place on the barrel 2 between the hub 5 and a shoulder 2c or enlarged portion of the distal end 2a of the barrel 2. In some embodiments, the hub 5 may have a portion below the proximal surface 5b having ribs that extend into the gaps 130 between the fingers 128 further preventing rotation of the collar 114.

Figure 12:
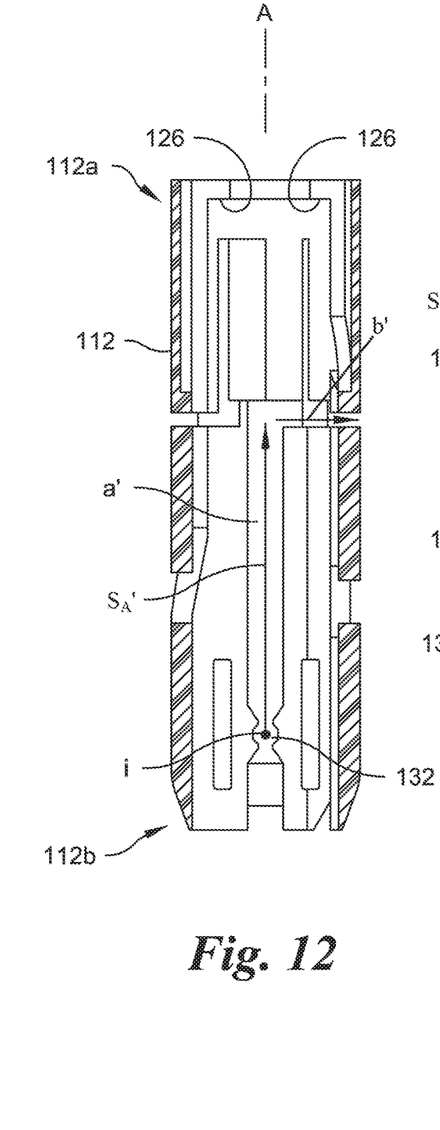
FIG. 12 is a front cross-sectional view of the outer tube of the safety device of FIG. 8.

Referring to FIGS. 12 and 13, in a preferred embodiment, the track S' has a plurality of segments, each segment corresponding to a relative position of the outer tube 112 with respect to the distal end 2a of the barrel 2 and/or to the cannula 3 projecting from the hub 5.

An assembly track segment $S_A'$ is provided to allow the safety device 100 to be assembled and inspected after the collar 114 has been attachment to the distal end 2a of the barrel 2 as discussed above. The assembly track segment $S_A'$ extends from a staging position (i) having an assembly catch 132 to a pre-injection position (ii) having a first catch 134 and has as a profile an initial portion a' substantially parallel to the longitudinal axis A of the outer tube 112 followed by a circumferential portion b' terminating in the first catch 134 in registry with the radially disposed ramp 140 on the flexible tongue 138 of the outer tube 112. When the collar 114 is attached to the distal end 2a of the barrel 2 and the pin 118 is in the staging position (i), the proximal end 112b of the outer tube 112 is in a position relative to the distal end 2a of the barrel 2 allowing the barrel 2 to be inspected.

During the assembly process, the force member or coil spring 116 is inserted in the outer tube 112. The collar 118, attached to the distal end 2a of the barrel 2, is then inserted in the outer tube 112 such that the pins 118 are in the assembly catch 132 at the staging position (i). The outer tube 112 is moved in the proximal direction causing the force member or coil spring 116 to be compressed as the pins 118 travel the length of the initial portion a' of the assembly track segment $S_A'$. The outer tube 112 is then rotated to move the pins 118 along the circumferential portion b' until the pins 118 become releasably retained in the first catch 134 thereby securing the outer tube 112 in the pre-injection position (ii). When the collar 114 is attached to the distal end 2a of the barrel 2 and the pin 118 is in the first catch 134, the cannula 3 extends a first length $L_1$ beyond the distal end 112a of the outer tube 112.

A first track segment $S_1'$, contiguous with the assembly track section $S_A'$, extends substantially parallel to the longitudinal axis A of the outer tube 112 from the pre-injection position (ii) to the full-insertion position (iii) of the outer tube 112. At the initiation of an injection, the distal end 112a of the outer tube 112 makes contact with the skin. The force applied by the skin to the outer tube 112 causes the flexible tongue 138 to deflect radially outwardly as the pin 118 moves out of the assembly catch 132, up the radially disposed ramp 140 and along the first track segment $S_1'$. As the skin is being penetrated by the cannula 3, continued application of force by the skin to the outer tube 112 further moves the outer tube 112 in the proximal direction and the pins 118 in the distal direction along the first track segment $S_1'$, to the full-insertion position (iii). When the collar 114 is attached to the distal end 2a of the barrel 2 and the pin 118 is in the full-insertion position (iii), the cannula 3 extends a second length $L_2$ greater than the first length $L_1$ from the distal end 112a of the outer tube 112. The first track segment $S_1'$, guides the pin 18 along a path substantially parallel to the longitudinal axis A of the outer tube 112. The outer tube 112 remains in the full-insertion position (iii) until withdrawal of the cannula 3 is initiated, typically after a full dose of the medicament is delivered.

A second track segment $S_2'$, contiguous with the first track segment $S_1'$, has a profile having an initial portion c' extending from the fully inserted position (iii) substantially parallel to the longitudinal axis A of the outer tube 112 to a mid portion d' having a first extent $d_1'$ angled with respect to the longitudinal axis A followed by a second extent $d_2'$ parallel to the longitudinal axis A. The mid portion d' is followed by a final portion e' having an arcuate profile providing a cammed surface terminating in an axially extending locked position (iv).

After a full dose of the medicament has been delivered, and withdrawal of the cannula 3 is initiated, the force applied by the skin to the outer tube 112 decreases. Under the reactive force of the compressed force member or coil spring 116, the outer tube 112 moves in the distal direction. The pins 118 move in the proximal direction along the second track segment $S_2'$ which guides the pins 118 in the initial portion c' substantially parallel to the longitudinal axis A imparting to the outer tube 112 translation in the axial direction without rotation. The first extent $d_1'$ of the mid portion d' cams the pins 118 in a direction angled with respect to the longitudinal axis A imparting to the outer tube 112 translation in the axial direction with rotation. The second extent $d_2'$ of the mid portion d' guides the pins 118 substantially parallel to the longitudinal axis A imparting to the outer tube 112 translation in the axial direction without rotation. The final portion e' of the second track segment $S_2'$ guides the pins 118 in a generally arcuate path imparting to the outer tube 112 both axial translation and a rotation until the pins 118 are in the locked position (iv) in the second catch 136. In the locked position, the outer tube 112 is fully extended covering the cannula 3 in the entirety and is prevented from moving in the distal or proximal directions.

The foregoing detailed description of the invention has been disclosed with reference to specific embodiments. However, the disclosure is not intended to be exhaustive or to limit the invention to the precise forms disclosed. Those skilled in the art will appreciate that changes could be made to the embodiments described above without departing from the broad inventive concept thereof. Therefore, the disclosure is intended to cover modifications within the spirit and scope of the present invention as defined by the appended claims.

We claim:

1. A needle safety device for an injection device having a generally cylindrical barrel with a shoulder from which a hub extends, the hub having a proximal surface spaced from the shoulder, a cannula extending distally from the hub, the needle safety device comprising:

an outer tube within which the barrel is moveable, the outer tube having a distal end, a proximal end spaced from the distal end, a circumferential step extending radially inwardly from an inner surface of the outer tube near the distal end and a longitudinal axis;

a track formed in the outer tube having a first catch, a first track segment, a second track segment and a second catch;

a collar disposed in the outer tube having a bore, the collar moveable in translation and rotation relative to the outer tube, wherein the collar is rotatable about the hub when the collar is attached to the hub, the collar including a channel at a distal end of the collar, a pin extending radially outwardly from the collar, the pin slideably engaging the track, the collar being sufficiently compliant and sized to allow passage of the hub and then return to an initial configuration to attach the collar to the barrel, the pin positioned in the first catch when the needle safety device is in a pre-injection position, the pin moving from the pre-injection position toward the distal end of the outer tube along the first track segment to a full-insertion position as skin of a patient is being penetrated by the cannula, the pin then moving from the full-insertion position toward the proximal end of the outer tube along the second track segment to a locked position when the cannula is removed from the skin, the pin positioned in the second catch in the locked position, the second track segment including a second extent extending substantially parallel to the longitudinal axis and a final portion between the second extent and the second catch that imparts both axial translation and rotation between the pin and the outer tube;

a coil spring positioned within the outer tube, the coil spring including a proximal end positioned on the channel and a distal end positioned on the circumferential step, the coil spring biasing the outer tube in a distal direction relative to the collar; and a removable shield that selectively covers the cannula in a mounted configuration, the coil spring positioned radially inwardly relative to the inner surface, the removable shield positioned radially inwardly relative to the coil spring in the initial configuration.

2. The needle safety device according to claim 1, wherein the collar has a generally hollow, tubular shape, the collar having a proximal end, the distal end having a plurality of spaced-apart fingers, the plurality of spaced-apart fingers being sufficiently flexible radially to allow passage of the hub through the bore to rotatably engage the hub and to abut the proximal surface when the hub is inserted in the bore; and the pin extends from a sidewall of at least one of the plurality of spaced-apart fingers.

3. The needle safety device according to claim 1, wherein the collar has a general shape of a hollow cylinder terminating at the distal end with an annulus having the bore sized to receive and retain the hub.

4. The needle safety device of claim 1, wherein the collar includes a plurality of spaced-apart fingers.

5. The needle safety device of claim 4, wherein the plurality of spaced-apart fingers is comprised of four fingers.

6. The needle safety device of claim 4, wherein a gap is located between each adjacent fingers of the plurality of spaced-apart fingers.

7. The needle safety device of claim 1, wherein the pin is comprised of two diametrically opposed pins.

8. The needle safety device of claim 1, wherein the track includes an assembly track segment, the assembly track segment configured to allow the safety device to be assembled and inspected.

9. The needle safety device of claim 8, wherein the assembly track segment has an initial portion extending substantially parallel to the longitudinal axis and a circumferential portion angled with respect to the longitudinal axis, the assembly track segment extending from a staging position to the pre-injection position.

10. The needle safety device of claim 9, wherein the assembly track segment includes an assembly catch, the pin positioned in the assembly catch in the staging position.

11. The needle safety device of claim 1, wherein the first track segment extends substantially parallel to the longitudinal axis.

12. The needle safety device of claim 1, wherein the outer tube includes a flexible tongue, the flexible tongue deflecting radially outwardly as the pin moves along the first track segment.

13. The needle safety device of claim 1, wherein the first track segment is continuous with the second track segment.

14. The needle safety device of claim 1, wherein the second track segment includes a profile having an initial portion extending from the full-insertion position substantially parallel to the longitudinal axis.

15. The needle safety device of claim 14, wherein the profile of the second track segment also includes a mid portion having a first extent angled with respect to the longitudinal axis.

16. The needle safety device of claim 1, wherein the outer tube is fully extended and covers the cannula in the locked position and is substantially prevented from moving in the distal and proximal directions.

\* \* \* \* \*